United States Patent [19]

Oppenheimer

[11] 4,000,644
[45] Jan. 4, 1977

[54] METHOD AND APPARATUS FOR TESTING TENSILE PROPERTIES

[76] Inventor: Edgar D. Oppenheimer, 527 Shore Acres Drive, Mamaroneck, N.Y. 10543

[22] Filed: Aug. 20, 1975

[21] Appl. No.: 605,986

[52] U.S. Cl. .................................... 73/95; 73/103
[51] Int. Cl.² ........................................ G01N 3/08
[58] Field of Search ............. 73/95, 101, 102, 103, 73/88.5 R

[56] References Cited

UNITED STATES PATENTS

| 3,853,000 | 12/1974 | Barnett et al. | 73/88.5 R |
| 3,878,711 | 4/1975 | Randolph | 73/88.5 R |

FOREIGN PATENTS OR APPLICATIONS

| 1,102,104 | 10/1955 | France | 73/95 |

Primary Examiner—James J. Gill
Assistant Examiner—Anthony V. Ciarlante
Attorney, Agent, or Firm—Robert H. Epstein

[57] ABSTRACT

A single ligament specimen is used to test the tensile properties in the short transverse direction of metal plate. A method of testing the specimen includes holding the specimen on one side of the ligament stationary and applying force to the other side of the specimen to elongate the ligament, and apparatus for implementing the method includes a fixture, a stationary clamp in the fixture, a movable clamp slidably mounted in the fixture, a load cell for measuring applied force to the movable clamp to elongate the ligament of the specimen, and a displacement transducer for measuring elongation.

11 Claims, 7 Drawing Figures

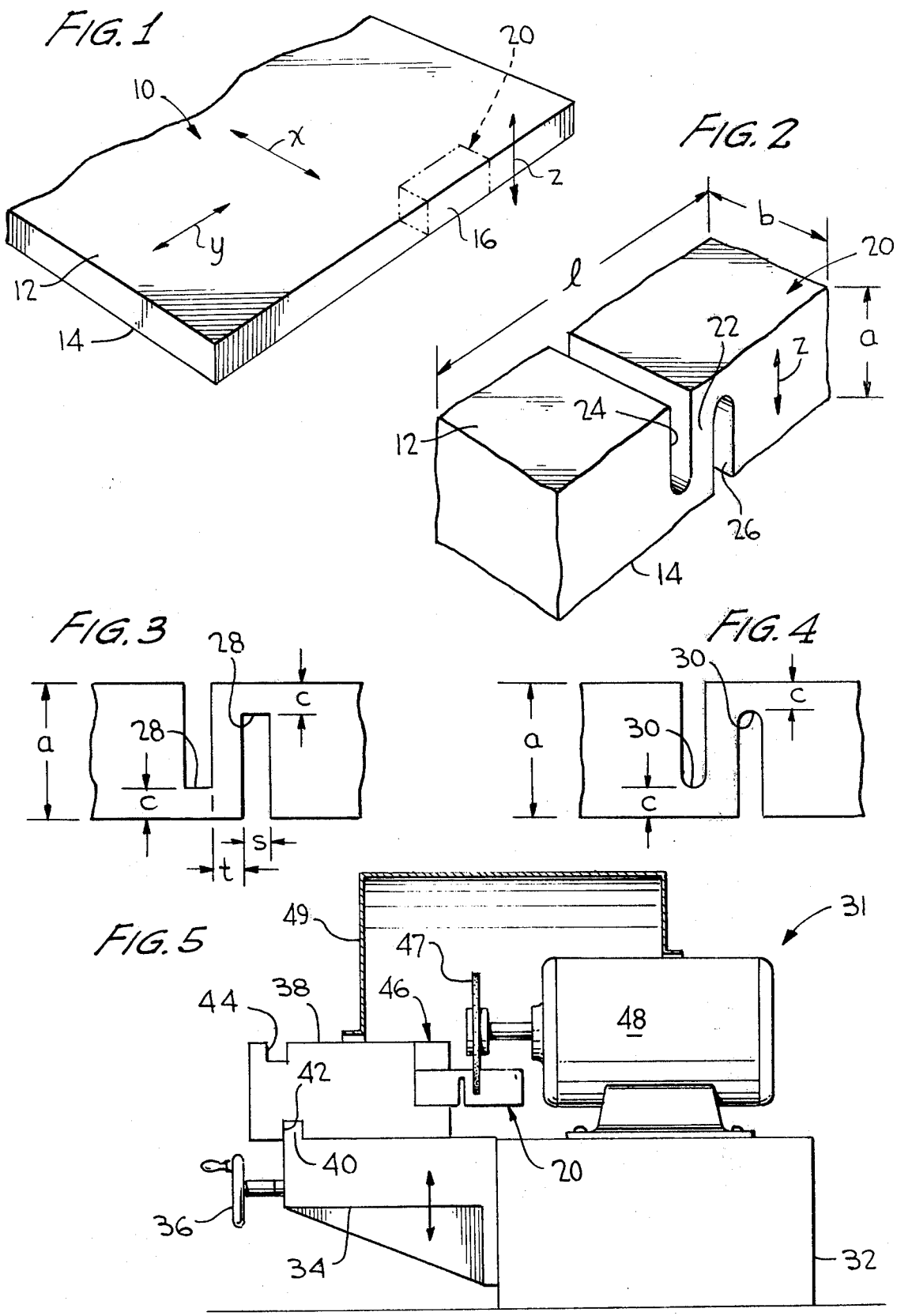

METHOD AND APPARATUS FOR TESTING TENSILE PROPERTIES

BACKGROUND OF THE INVENTION

1. Field of the Invention

The present invention pertains to the testing of engineering materials and, more particularly, to the testing of tensile properties of metal plate.

2. Discussion of the Prior Art

Interest in the anisotropy of engineering materials and, particularly, the current problems of lamellar tearing of rolled steel plate, as noted in "Commentary on Highly Restrained Welded Connections," AISC Engineering Journal, 3rd Quarter 1973, "Lamellar Tearing and the Slice Bend Test," M. L. Drury and J. E. M. Jubb, Welding Journal, Feb. 1973, "A Quantitative Weldability Test for Susceptibility to Lamellar Tearing," R. P. Oats and R. D. Stout, Welding Journal, Nov. 1973 and "Lamellar Tearing", J. E. M. Jubb, Welding Research Council Bulletin No. 168, Dec. 1971, make it highly desirable to have a simple, quick and reliable test to determine the ultimate tensile strength, the tensile yield strength and the tensile elongation before necking in the short transverse (Z) direction of steel plate to be welded in critical structural connections. It is especially desirable to have a test which can be performed on the site of fabrication or erection of large steel structures. Such a test should avoid difficult machining and joining procedures in the preparation of sample specimens and should employ test equipment small enough to be transported by passenger vehicles.

In the past, a variety of test sample designs and procedures have been employed by different research workers to measure the short transverse properties of relatively thin rolled plate. For tensile tests, either the specimens are miniature tensile bars or have ends added by welding or brazing. Other tests employ simpler specimens which are shaped as rings, flat plates and the like, but such specimens do not provide information in terms of the conventional tensile properties desired by designers.

A double ligament tensile impact test was described in "Measurement of Short-Transverse Tensile-Impact Energy of Rolled Steel Plate," E. D. Oppenheimer and J. T. Berry, ASME Pressure Vessel and Piping Conference, 1968. The two-ligament design was necessary for impact testing in order that the restraining ligament forces on the center segment be balanced and, therefore, no guidance device be needed to prevent rotation of the center segment during fracture. The use of a guidance device, such as a restraining clamp with slide or the like, would add sufficient mass to the moving segment of the specimen to severely degrade the test results.

Further work on slow strain rate tensile ligament testing as described in "The Evaluation of Anisotropy and Plane Strain Properties of Cast and Wrought Materials," R. G. Kumble, PhD. Thesis, University of Vermont, May 1973 and "The Double Ligament Tensile Test: Its Development and Application," E. D. Oppenheimer, R. G. Kumble and J. T. Berry, ASME Winter Annual Meeting, Nov. 1974, was performed using the original double ligament specimens because tooling and specimens existed and the design was suited to research work on very thin (¼ inch) plate. However, while the results were excellent, this specimen has obvious practical drawbacks when applied to industrial problems such as on-site use, simple preparation of specimens of small size, as set forth above. Further disadvantages stem from the fact that, even when the specimens are of larger size, it is essential that close tolerances be held so that both ligaments are, as nearly as possible, of equal strength. Close dimensional control of the location of the ligaments with respect to each other must be exercised. For common structural sizes, for example 1 inch thick plate, the test apparatus becomes very bulky and heavy.

SUMMARY OF THE INVENTION

Accordingly, it is a primary object of the present invention to overcome the above-mentioned disadvantages of the prior art by providing method and apparatus for testing tensile properties of engineering metal materials, such as rolled steel plate, using a single ligament specimen.

Another object of the present invention is to facilitate the forming of a specimen for testing tensile properties of metal plate by requiring the formation of only a single ligament in the specimen.

An additional object of the present invention is to provide a tensile properties test for metal plate wherein specimens for testing short, transverse direction properties can be quickly and economically cut from plate without requiring that the sides of the specimen be smooth and parallel.

The present invention has a further object in that a method of testing tensile properties of metal plate requires only a single ligament to be formed in a specimen with the portion of the specimen on one side of the ligament held stationary and the portion of the specimen on the other side of the ligament moved under a controlled force.

Yet another object of the present invention is to produce a specimen for testing to determine tensile properties in the short transverse direction of metal plate, the specimen having a ligament defined by parallel slots with rounded ends to improve stress distribution during testing.

An additional object of the present invention is to use a stationary clamp and a movable clamp in a simple, light weight fixture for testing tensile properties of metal materials.

Some of the advantages of the present invention over the prior art, particularly the double ligament tensile test, are that the use of a single ligament specimen permits wider tolerances in machining since there is no requirement for two identical ligaments. Moreover, forming only a single ligament reduces specimen preparation time since not only are additional slots not required but the relative location of the single ligament along the specimen bar is not critical, and the test apparatus is significantly smaller and lighter in weight due to the decreased length of the specimen bars and the need for only two clamps thereby rendering the method and apparatus of the present invention suitable for on-site use.

The present invention is generally summarized in a method of testing the tensile properties of metal being normally in the form of plate in the short transverse direction comprising the steps of cutting a specimen bar from the plate, slotting the specimen bar from opposite surfaces to form a ligament extending in the short transverse direction, clamping the slotted specimen bar on one side of the ligament with a stationary clamp, clamping the slotted specimen bar on the opposite side of the ligament with a movable clamp, and applying a force to move the movable clamp relative to the stationary clamp to elongate the ligament. The present invention is further generally summarized in apparatus for testing the tensile strength of a specimen of a metal body normally in the form of plate having first and second sides separated by a ligament comprising a fixture including stationary clamp means for holding the first side of the specimen stationary, movable clamp means movably associated with said fixture relative to said stationary clamp means for gripping the second side of the specimen, and force applying means for applying a force to said movable clamp means to move said movable clamp means relative to said stationary clamp means and elongate the ligament of the specimen.

The present invention is particularly suited to the testing of the tensile properties of rolled steel plate; however, it has applicability to the testing of all metal plate as well as metal bodies in other forms.

Other objects and advantages of the present invention will become apparent from the following description of the preferred embodiment taken in conjunction with the accompanying drawings.

BRIEF DESCRIPTION OF THE DRAWINGS

FIG. 1 is a broken perspective of a portion of a rolled steel plate to be tested in accordance with the method and apparatus of the present invention.

FIG. 2 is a perspective of a single ligament specimen for testing in accordance with the present invention.

FIGS. 3 and 4 are side elevations of specimens according to the present invention utilizing squared end and rounded end slots, respectively.

FIG. 5 is a side elevation of apparatus for forming a specimen according to the present invention.

DESCRIPTION OF THE PREFERRED EMBODIMENT

Figure 6:
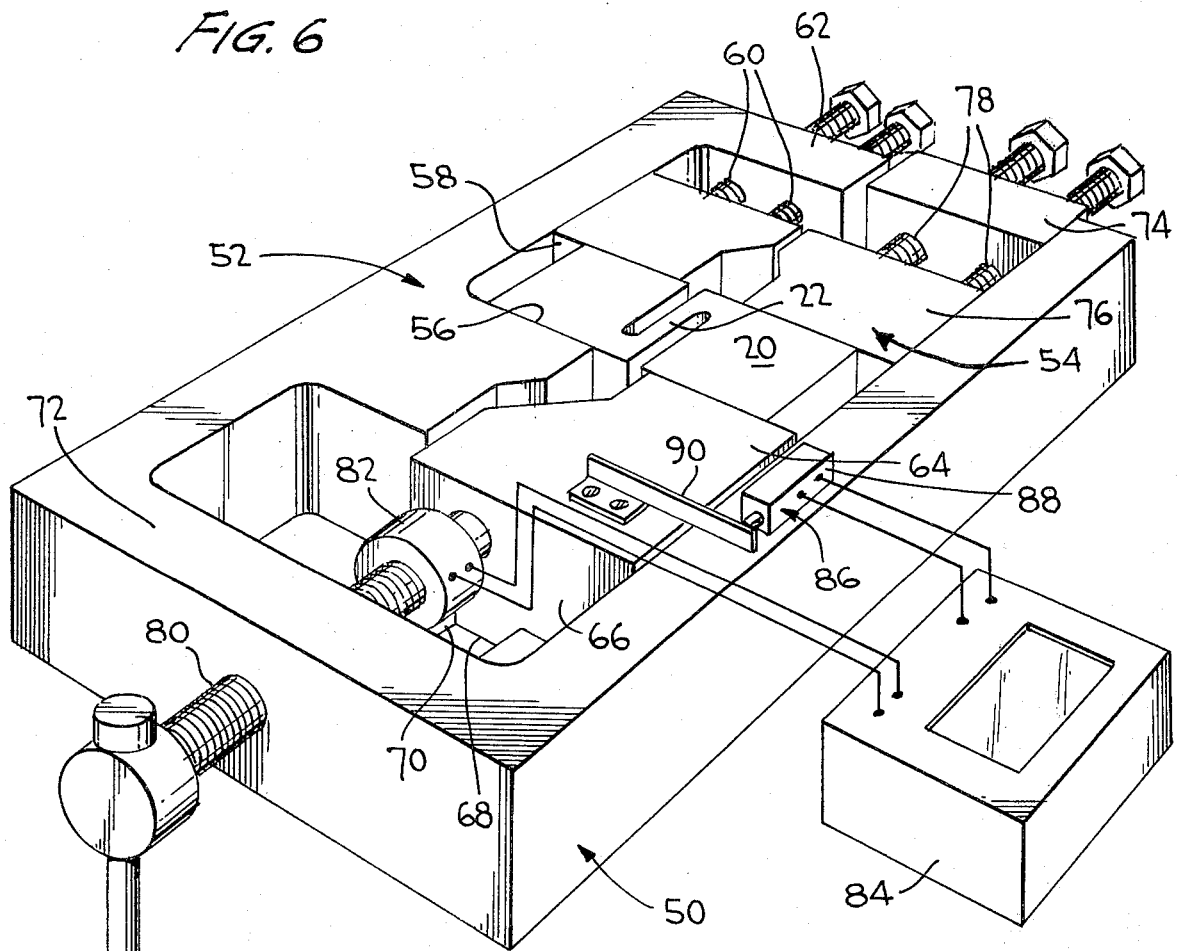
FIG. 6 is perspective of apparatus for testing a specimen in accordance with the present invention.

A portion of a rolled steel plate 10 to be tested for tensile strength is shown in FIG. 1 with the rolling direction indicated by arrow $x$, the transverse direction indicated by arrow $y$ and the short transverse direction indicated by arrow $z$ to define, for reference purposes, rolling surfaces 12 and 14, and a transverse surface 16.

A specimen 20 in the form of a bar is cut such as by flame-cutting from a suitable location on the rolled plate 10, such as from the portion shown in phantom in FIG. 1, the sides and ends being left rough. Any beads, burrs or droplets can be removed from the edges of the specimen bar with suitable hand tools. The solid specimen bar 20 is slotted to define a single ligament 22 between narrow, parallel slots 24 and 26 extending from rolling surfaces 12 and 14, respectively, as shown in FIG. 2 such that the ligament 22 extends in the short transverse direction $z$. The slots 24 and 26 can be cut with a milling cutter which can form squared ends 28 for the slots, as shown in FIG. 3; or, preferably and more practically for portable apparatus, the slots 24 and 26 can be cut with an abrasive wheel to provide rounded ends 30 for the slots, as shown in FIGS. 2 and 4. The rounded end configuration for the slots is preferred since it provides better stress distribution in the specimen.

The proportions of specimens to be tested should be retained throughout the expected range of specimen sizes and materials. One example of recommended values is as follows:
$s = (0.05$ to $0.10)a$    $t = (0.75$ to $1.5)s$ $c = (2.5$ to $5.0)t$    $l = (3$ to $8)a$ where
  $s$ is slot width
  $a$ is thickness of specimen
  $c$ is distance between slot end and opposite rolling surface
  $t$ is thickness of ligament
  $l$ is length of specimen Apparatus 31 for slotting the specimen bar 20 is illustrated in FIG. 5 and includes a base 32 having a table 34 mounted thereon for vertical movement by rotation of a crank wheel 36 cooperating with a conventional mechanism for raising and lowering the table 34 relative to base 32. A fixture 38 is mounted on table 34 and preceisely positioned relative thereto by means of an upward extending tongue 40 on table 34 received in either of offset grooves 42 or 44 in the bottom and top of the fixture. The fixture 38 has a clamp 46 disposed along the rear thereof adapted to firmly hold a specimen bar 20 during slotting by an abrasive slotting wheel 47 rotated by an electric motor 48 mounted on the base 32. A hood 49 extends over the slot cutting area.

In order to cut the slots 24 and 26 in a specimen bar 20, the specimen bar is mounted on the fixture 38 by means of clamp 46; and, once the specimen bar is placed in the clamp 46, both slots 24 and 26 can be cut without removing the bar by inverting the fixture. That is, the clamp 46 grips an end of the specimen bar 20 such that the first slot can be cut by horizontal movement of the fixture 38 relative to the abrasive slotting wheel 47 while tongue 40 engages groove 44; and, thereafter, the second slot can be cut by inverting the fixture 38 to position tongue 40 in groove 42, as shown in FIG. 5. The horizontal offset of groove 42 relative to groove 44 corresponds to the desired thickness for the ligament 22 and, therefore, the spacing between slots; and, thus once the fixture is inverted, the operator need only commence horizontal movement of the fixture 38 again to cut the second slot. Accordingly, it will be appreciated that a specimen bar can be quickly, easily and accurately cut with the apparatus 31, and the depth of cut need only be adjusted by the operator as the slotting wheel wears.

Apparatus for testing the single ligament specimen bar 20 is shown in FIG. 6 and includes a fixture 50 having a generally rectangular configuration. Within the fixture 50 are a stationary clamp 52 and a movable clamp 54. The stationary clamp is formed on a fixed jaw 56 integral with the fixture and a clamping jaw 58 movable within a recess in the fixture by means of a pair of clamping screws 60 extending through and engaging an end wall 62 of the fixture. The movableclamp 54 is formed of a movable jaw 64 mounted on a slide 66 having a key or runner 68 received in a keyway 70 in the bottom of the fixture 50 extending between end wall 62 and an opposite end wall 72. The end wall 62 is cut away to accommodate a block 74 extending from the slide 66, and a clamping jaw 76 is disposed between block 74 and jaw 64 and is movable therebetween by means of a pair of clamping screws 78 extending through and engaging the block 74. A jack screw 80 engages end wall 72 of the fixture and mounts internally of the fixture a load cell 82 adapted mechanically, or in other suitable manner to measure the applied force to the slide 66 by operating the jack screw. Alternate means of applying controllable force between the fixture wall 72 and the slide 66 include but are not limited to an hydraulic cylinder in place of the jack screw 80.

The load cell 82 supplies electrical, hydraulic, or other output signals corresponding to force to a conventional X-Y plotter 84. Similarly, a displacement transducer 86 supplies output signals corresponding to movement of the slide 66, and therefore elongation of the specimen ligament 22 to the X-Y plotter 84. The displacement transducer has a fixed member 88 attached to the fixture and a movable member 90 mounted on slide 60. The displacement transducer can be of any conventional construction having adequate sensitivity.

In operation, the jaw 64 of movable clamp 54 is aligned with the fixed jaw 56 of stationary clamp 52 by adjustment of jack screw 80, and an end of the single ligament specimen 20 is clamped between jaws 56 and 58 by tightening clamp screws 60 and between jaws 64 and 76 by tightening clamp screw 78. Force can now be applied from the jack screw 80 through load cell 82 to the specimen 20 via the slide 66 to produce tensile failure in the ligament 22 of the specimen. Useful results can be derived merely from observing the total elongation before failure of the ligament or the extent of necking or the reduction of area in the fracture. However, the most useful information is derived from simultaneous measurement of the force applied to the ligament through the load cell 82 and the elongation of the ligament which is measured as the relative displacement of the stationary and movable clamps by the displacement transducer 86. Correction must be made for the elastic compliance of the fixture, but this can be determined experimentally using an unslotted bar as described in the above mentioned article, "The Double Ligament Tensile Test: Its Development and Application," E. D. Oppenheimer, R. G. Kumble and J. T. Berry, ASME Winter Annual Meeting, November 1974. Paper No. 74-WA/Mat-6.

Figure 7:
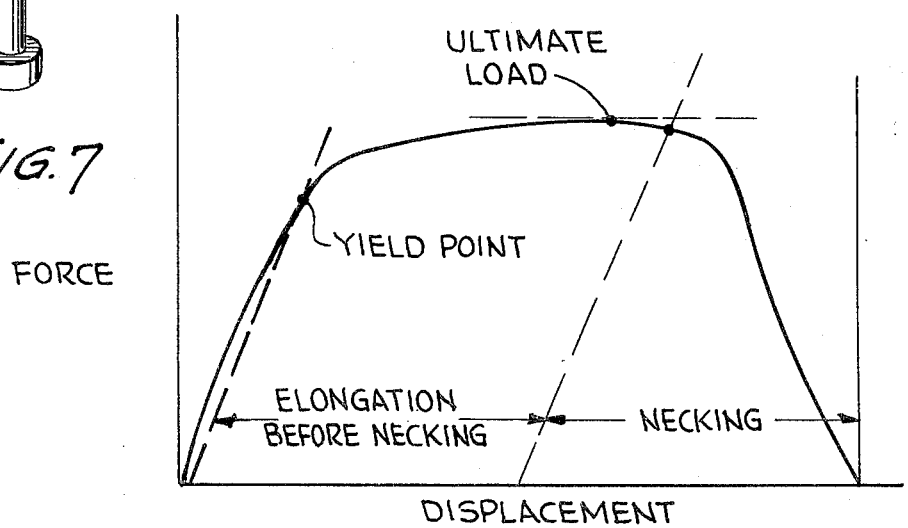
FIG. 7 is a plot of force against displacement for a specimen tested in accordance with the present invention.

The force and displacement sensors are connected to the X-Y plotter 84 which draws a chart, as shown in FIG. 7. Analysis of this chart together with dimensions taken from the specimen before testing permit simple calculations of ultimate strength, yield strength, and elongation before necking.

From the above, it will be appreciated that not only is the specimen according to the present invention easy to form but, by forming the specimen with side portions connected by the single ligament 22, the side portions can be easily gripped by the stationary and movable clamps for testing. To this end, the present invention is highly advantageous over the prior art because the specimen is gripped immediately on opposite sides of the ligament to be elongated and the size and bulk of the testing fixture is sufficiently reduced to permit the testing apparatus to be used for on-site applications. The side portions can have any configuration as long as they can be securely gripped by the clamps.

Inasmuch as the present invention is subject to many variations, modifications and changes in detail, it is intended that all subject matter described above or shown in the accompanying drawings be interpreted as illustrative and not in a limiting sense.

What is claimed is:

1. A method of testing the tensile properties of a metal body in the short transverse direction comprising the steps of
    cutting a specimen bar from the metal body;
    forming a single ligament extending in the short transverse direction of the specimen bar by forming a first slot in one surface of the specimen bar and forming a second slot in the opposite surface of the specimen bar;
    clamping the slotted specimen bar on one side of the ligament with a stationary clamp positioned outwardly adjacent to said first slot and against the surface in which the first slot is formed so as to apply a force against said surface outwardly of the first slot;
    clamping the slotted specimen bar on the opposite side of the ligament with a movable clamp positioned outwardly adjacent to said second slot and against said opposite surface in which the second slot is formed so as to apply a force against said opposite surface outwardly of the second slot; and
    applying a force to the movable clamp relative to the stationary clamp to elongate the single ligament.

2. A method as recited in claim 1 in which the specimen bar is cut from rolled plate.

3. A method as recited in claim 2 in which the plate is steel.

4. A method as recited in claim 1 and further comprising the step of measuring the force applied and the elongation of the ligament.

5. A method as recited in claim 1 wherein said slotting step includes forming a pair of parallel slots in the specimen bar defining the ligament with an abrasive wheel.

6. A method as recited in claim 1 wherein said slotting step includes forming a pair of parallel slots having rounded ends in the specimen bar to define the ligament.

7. Apparatus for testing the tensile properties of a specimen of metal plate having first and second sides separated by a ligament having a slot on one side and a slot on the opposite side of said ligament comprising
    a fixture including stationary clamp means for gripping the specimen adjacent one of the slots for holding the first side of the specimen stationary;
    movable clamp means movably associated with said fixture relative to said stationary clamp means for gripping the second side of the specimen adjacent to the other of said slots;
    force applying means for applying a force to said movable clamp means to move said movable clamp means relative to said stationary clamp means and elongate the ligament of the specimen; and means for measuring the force applied by said force applying means and the displacement of said movable clamp means relative to said stationary clamp means.

8. Apparatus as recited in claim 7 wherein said movable clamp means includes a slide slidably mounted in said fixture.

9. Apparatus as recited in claim 8 wherein said fixture has a guide channel extending therealong and said slide has a runner received in said guide channel.

10. A specimen for testing to determine tensile properties in the short transverse direction of metal plate having first and second parallel rolling surfaces comprising a bar cut from the plate having a first slot extending transversely from said first rolling surface and terminating at an end spaced from said second rolling surface, a second slot in parallel relation with said first slot extensing transversely from said second rolling surface and terminating at an end spaced from said first rolling surface, said first and second slots defining a single ligament therebetween extending in the short transverse direction whereby said ends provide improved stress distribution during testing and wherein the specimen has dimensions in accordance with the formula:

$s = (.05 \text{ to } .10)a \qquad t = (.75 \text{ to } 1.5)s$
$c = (2.5 \text{ to } 5.0)t \qquad l = (3 \text{ to } 8)a$ where
- $s$ is slot width
- $a$ is thickness of specimen
- $c$ is distance between slot end and opposite rolling surface
- $t$ is thickness of ligament
- $l$ is length of specimen.

11. A specimen as recited in claim 10 in which the slot ends are rounded.

* * * * *